United States Patent
Parent et al.

(10) Patent No.: US 9,547,897 B2
(45) Date of Patent: Jan. 17, 2017

(54) SYSTEM AND METHOD FOR PREDICTING SCOLIOSIS PROGRESSION

(71) Applicant: École De Technologie Supérieure, Montréal (CA)

(72) Inventors: Stefan Parent, Saint-Lambert (CA); Marie-Lyne Nault, Montreal (CA); Jean-Marc Mac-Thiong, Ville Mont-Royal (CA); Hubert Labelle, Laval (CA); Jacques De Guise, Montreal (CA)

(73) Assignees: ECOLE DE TECHNOLOGIE SUPERIEURE, Montreal (CA); VALORISATION HSJ, LIMITED PARTNERSHIP, Montreal (CA)

( * ) Notice: Subject to any disclaimer, the term of this patent is extended or adjusted under 35 U.S.C. 154(b) by 0 days.

(21) Appl. No.: 14/434,944

(22) PCT Filed: Oct. 15, 2013

(86) PCT No.: PCT/CA2013/000884
§ 371 (c)(1),
(2) Date: Apr. 10, 2015

(87) PCT Pub. No.: WO2014/056098
PCT Pub. Date: Apr. 17, 2014

(65) Prior Publication Data
US 2015/0287184 A1    Oct. 8, 2015

Related U.S. Application Data

(60) Provisional application No. 61/713,226, filed on Oct. 12, 2012.

(51) Int. Cl.
*G06T 7/00*    (2006.01)
*G06F 19/00*    (2011.01)
(Continued)

(52) U.S. Cl.
CPC ........... *G06T 7/0012* (2013.01); *A61B 5/1071* (2013.01); *A61B 5/4566* (2013.01); *G06F 19/345* (2013.01);
(Continued)

(58) Field of Classification Search
None
See application file for complete search history.

(56) References Cited

U.S. PATENT DOCUMENTS

2005/0020942 A1*  1/2005  Wada ............... A61B 5/4561
                                                     600/594
2007/0073194 A1*  3/2007  Chen ............... A61B 5/1075
                                                     600/594
(Continued)

OTHER PUBLICATIONS

Assessment of the 3-D Reconstruction and High-Resolution Geometrical Modeling of the Human Skeletal Trunk From 2-D Radiographic Images. S. Delorme, Y. Petit, J. A. de Guise, H. Labelle, C.-É. Aubin, and J. Dansereau. Aug. 2003.*
(Continued)

*Primary Examiner* — Stephen R Koziol
*Assistant Examiner* — Delomia L Gilliard
(74) *Attorney, Agent, or Firm* — Norton Rose Fulbright Canada LLP (57) ABSTRACT

There is described a system, method, and computer-readable medium having stored thereon executable program code for generating a final Cobb angle prediction for idiopathic scoliosis, the method comprising: receiving patient-specific 3D morphological spine parameters, a selected curve type, and a selected skeletal maturity; applying the patient-specific 3D morphological spine parameters, a selected curve type, and a selected skeletal maturity to a predictive model based on 3D morphological spine parameters, curve type, and skeletal maturity, and generating the final Cobb angle
(Continued)

prediction by modeling a progression curve of the idiopathic scoliosis.

20 Claims, 9 Drawing Sheets

(51) Int. Cl.
  *A61B 5/107*  (2006.01)
  *A61B 5/00*  (2006.01)
  *G06K 9/52*  (2006.01)
  *G06T 5/00*  (2006.01)

(52) U.S. Cl.
  CPC ............ *G06F 19/3437* (2013.01); *G06K 9/52* (2013.01); *G06T 5/001* (2013.01); *G06T 7/004* (2013.01); *G06T 2207/10116* (2013.01); *G06T 2207/30012* (2013.01)

(56) References Cited

U.S. PATENT DOCUMENTS

| | | | |
|---|---|---|---|
| 2009/0035772 A1* | 2/2009 | Nelson ................ | A61M 1/00 435/6.16 |
| 2009/0104620 A1* | 4/2009 | Schramm ............. | A61B 5/107 435/6.16 |
| 2009/0226055 A1* | 9/2009 | Dankowicz ........... | A61B 19/52 382/128 |
| 2013/0202179 A1* | 8/2013 | Illes ................... | A61B 5/1075 382/132 |

OTHER PUBLICATIONS

Personalized X-Ray 3-D Reconstruction of the Scoliotic Spine From Hybrid Statistical and Image-Based Models. Samuel Kadoury, Farida Cheriet and Hubert Labelle. Sep. 2009.*
Coronal plane segmental flexibility in thoracic adolescent idiopathic scoliosis assessed by fulcrum-bending radiographs. Hasler, Hefti and Buchler. Feb. 2010.*
Fong DY, Lee CF, Cheung KM, et al. A meta-analysis of the clinical effectiveness of school scoliosis screening. Spine (Phila Pa 1976). 2010;35:1061-1071.
Bunnell WP. The natural history of idiopathic scoliosis before skeletal maturity. Spine (Phila Pa 1976). 1986;11:773-776.
Lonstein JE, Carlson JM. The prediction of curve progression in untreated idiopathic scoliosis during growth. J Bone Joint Surg Am. 1984;66:1061-1071.
Weinstein SL, Dolan LA, Cheng JC, et al. Adolescent idiopathic scoliosis. Lancet, 2008;371:1527-1537.
Labelle H, Aubin CE, Jackson R, et al. Seeing the spine in 3D: how will it change what we do? Journal of pediatric orthopedics. 2011;31:S37-45.
Nault ML, Parent S, Phan P, et al. A modified Risser grading system predicts the curve acceleration phase of female adolescent idiopathic scoliosis. J Bone Joint Surg Am. 2010;92:1073-1081.
Guo X, Chau WW, Chan YL, et al. Relative anterior spinal overgrowth in adolescent idiopathic scoliosis. Results of disproportionate endochondral-membranous bone growth. The Journal of bone and joint surgery British volume. 2003;851026-1031.
Humbert L, De Guise JA, Aubert B, et al. 3D reconstruction of the spine from biplanar X-rays using parametric models based on transversal and longitudinal inferences. Med Eng Phys. 2009. 7.
Pomero V, Mitton D, Laporte S, et al. Fast accurate stereoradiographic 3D-reconstruction of the spine using a combined geometric and statistic model. Clin Biomech (Bristol, Avon). 2004;19:240-247.
Villemure I, Aubin CE, Grimard G, et al. Progression of vertebral and spinal three-dimensional deformities in adolescent idiopathic scoliosis: a longitudinal study. Spine. 2001;26:2244-2250.
Glaser DA, Doan J, Newton PO. Comparison of 3-Dimensional Spinal Reconstruction Accuracy: Biplanar Radiographs With EOS Versus Computed Tomography. Spine (Phila Pa 1976). 2012;37:1391-1397.
Stokes IA. Three-dimensional terminology of spinal deformity. A report presented to the Scoliosis Research Socieyy by the Scoliosis Research Society Working Group on 3-D terminology of spinal deformity. Spine. 1994;19:236-248.
Skogland LB, Miller JA. The length and proportions of the thoracolumbar spine in children with idiopathic scoliosis. Acta orthopaedica Scandinavica. 1981;52:177-185.
Parent S, Labele H, Skalli W, et al. Vertebral wedging characteristic changes in scoliotic spines. Spine. 2004;29:E455-462.
Kouwenhoven, JWM; Castelein, RM: Adapted from: The pathogenesis of adolescent idiopathic scoliosis—Spine 2007, pp. 34-58.
Aubin CE, Dansereau J, Petit Y, et al. Three-dimensional measurement of wedge scoliotic vertebrae and intervertebral disks. Eur Spine J. 1998;7:59-65.
Lonstein, JE: Adolescent idiopathic scoliosis: Screening and diagnosis. Instructional Course Lectures 38:105-113. Edited by Barr JS. American Academy of Orthopaedic Surgeons, Chicago, 1989.
Weinstein, S.I.; Dolan, L.A.; Spratt, K.F.; Peterson, K.K, Spoonarmore, M.J.; Ponseti, I.: Health and Functioning in Idiopathic Scoliosis, JAMA, 2003, vol. 289, No. 5, pp. 559-567.
Wong,H-K; Tan, K-J: The natural history of adolescent idiopathic scoliosis. Indian J Orthop, 2010 Jan. Mar. 2010; 44(1): 9-13.

* cited by examiner

SYSTEM AND METHOD FOR PREDICTING SCOLIOSIS PROGRESSION

CROSS-REFERENCE TO RELATED APPLICATIONS

The present patent application is a US National Stage of International Application No. PCT/CA2013/000884, filed on Oct. 15, 2013, which claims priority under 35 USC §119(e) of U.S. provisional Application Ser. No. 61/713,226, filed on Oct. 12, 2012, the contents of which are hereby incorporated by reference.

FIELD OF THE INVENTION

The present invention relates to methods for evaluating scoliosis prognosis. In particular, the present invention relates to methods and systems for predicting the progression of scoliosis, stratifying a subject having a scoliosis and assessing the efficacy of a brace on a subject having a scoliosis.

BACKGROUND

Spinal deformities and scoliosis in particular, represent the most prevalent type of orthopedic deformities in children and adolescents. Adolescent idiopathic scoliosis (AIS) is a three-dimensional spinal deformity with a prevalence of 1.34% in children between 6 and 17 years old for a Cobb angle of 10° or more.

Classical risk factors such as skeletal maturity, initial Cobb angle and type of curvature were found to predict final Cobb angle but to a certain extent only. There is still no reliable method to predict whether an individual's curve will progress and how severe the progression will be. Current treatments are only available to patients with a curvature>25°.

The only treatment available today for patients with a moderate curvature (<40° but >25°) is external bracing. Bracing never corrects a curve but rather stabilizes the curve during the time an adolescent is growing, although its effectiveness is questionable (50% of those wearing a brace simply do not benefit). It has also been shown that bracing typically proves ineffective on two (2) patients out of three (3). For patients with a curvature >40°, the current option is the surgical correction.

Unfortunately, there is no proven method available to identify which affected children or adolescents may require treatment based on the risk of progression. Consequently, the application of current treatments is delayed until a significant deformity is detected or until a significant progression is clearly demonstrated, resulting in a delayed and less optimal treatment. Also, the uncertainty related to curve progression and outcome creates anxiety for families and patients with scoliosis as well as unnecessary psychosocial stresses associated with brace treatment. The failure to accurately predict the risk of progression can also lead to inadequate treatment, as well as unnecessary medical visits and radiographs.

There is thus a need for a method of predicting the scoliosis curve progression, particularly in treatment decisions for individuals who are diagnosed with scoliosis.

SUMMARY

There is described herein a method and system for predicting scoliosis curve progression based on measuring a combination of predictive factors. A predictive model is created based on type of curvature, skeletal maturity and three-dimensional (3D) spine parameters. The predictive model may thus enable early prognosis of scoliosis, stratifying of subjects having a scoliosis as well as early clinical intervention to mitigate progression of the disease. It may also allow selection of subjects for clinical trials involving less invasive treatment methods.

The 3D spine parameters are selected from one or more of the six categories of 3D measurements or parameters: angle of plane of maximum curvature, initial Cobb angles (kyphosis, lordosis), 3D wedging (apical vertebra, apical disks), rotation (upper and lower junctional vertebra, apical vertebra, thoracolumbar junction and mean peri-apical intervertebral) rotation, torsion (geometrical and/or mechanical torsion) and slenderness (height/width ratio).

In accordance with a broad aspect, there is provided a system for generating a final Cobb angle prediction for idiopathic scoliosis, the system comprising a memory having stored thereon a predictive model based on 3D morphological spine parameters, curve type, and skeletal maturity; a processor; and at least one application stored in the memory and executable by the processor for receiving patient-specific 3D morphological spine parameters, a selected curve type, and a selected skeletal maturity, retrieving the predictive model, and modeling a progression curve of the idiopathic scoliosis to generate the final Cobb angle prediction.

In some embodiments, the at least one application is further configured to receive two-dimensional spine data, reconstruct a three-dimensional spine morphology, and extract the patient-specific 3D morphological spine parameters therefrom.

In some embodiments, the patient-specific 3D morphological spine parameters comprise at least one of an initial Cobb angle, a plane of maximal deformation, a three-dimensional wedging of vertebral body and disk, an axial intervertebral rotation of an apex, upper and lower junctional level and thoracolumbar level, slenderness, and torsion.

In some embodiments, the at least one application is executable by the processor for computing the initial Cobb angle in at least one of a frontal plane of the reconstructed three-dimensional spine morphology, a sagittal plane of the reconstructed three-dimensional spine morphology, and the plane of maximal deformation.

In some embodiments, the at least one application is executable by the processor for applying the patient-specific 3D morphological spine parameters, the selected curve type, and the selected skeletal maturity to the retrieved predictive model for modeling the progression curve from the initial Cobb angle to a predicted final Cobb angle, the predicted final Cobb angle indicative of a forecasted evolution of the idiopathic scoliosis at the selected skeletal maturity.

In some embodiments, the at least one application is executable by the processor for computing the plane of maximal deformation as a plane in the reconstructed three-dimensional spine morphology having an axial angle that extends around a direction in which the initial Cobb angle is maximal.

In some embodiments, the at least one application is executable by the processor for computing three-dimensional wedging of junctional and peri-apical disk levels of the reconstructed three-dimensional spine morphology, and a sum of three-dimensional wedging of all thoracic and lumbar disks of the reconstructed three-dimensional spine morphology.

In some embodiments, the at least one application is executable by the processor for computing the axial intervertebral rotation of a superior vertebra of the reconstructed three-dimensional spine morphology relative to an inferior vertebra of the reconstructed three-dimensional spine morphology, the inferior vertebra adjacent the superior vertebra and the superior and inferior vertebrae each having defined therefor in the reconstructed three-dimensional spine morphology a local axis plane comprising a first axis, the rotation computed by projecting the first axis of the superior vertebra onto the local axis plane of the inferior vertebra.

In some embodiments, the at least one application is executable by the processor for computing the slenderness as a ratio of a height to a width of a body of each one of thoracic and lumbar vertebrae of the reconstructed three-dimensional spine morphology.

In some embodiments, the at least one application is executable by the processor for receiving the patient-specific 3D morphological spine parameters comprising at least one of a mechanical torsion and a geometrical torsion.

In some embodiments, the at least one application is executable by the processor for calculating the mechanical torsion by computing a first sum of the axial intervertebral rotation for all vertebrae in a first hemicurvature of a main idiopathic scoliosis curve in the reconstructed three-dimensional spine morphology, a second sum of the axial intervertebral rotation for all vertebrae in a second hemicurvature of the main curve, and a mean of the first sum and the second sum, the first hemicurvature defined between an upper end vertebra and an apex of the main curve and the second hemicurvature defined between a lower end vertebra of the main curve and the apex.

In some embodiments, the at least one application is executable by the processor for receiving the selected curve type comprising one of single right thoracic, double with main thoracic, double with main lumbar, triple, single left thoracolumbar, single left lumbar, and left thoracic-right lumbar.

In some embodiments, the at least one application is executable by the processor for receiving the selected skeletal maturity comprising skeletal maturity data indicative of one of a first stage skeletal maturity and a second stage skeletal maturity, the first stage skeletal maturity characterized by an open triradiate cartilage with a Risser grade equal to zero and the second stage skeletal maturity characterized by one of a Risser grade equal to one and a closed triradiate cartilage with a Risser grade equal to zero.

In some embodiments, the memory has stored therein a plurality of treatment options each suitable for treating the idiopathic scoliosis and having associated therewith at least one of a range of final Cobb angles and a rate of change of idiopathic scoliosis curve progression, and further wherein the at least one application is executable by the processor for querying the memory with at least one of the final Cobb angle prediction and the modelled progression curve to retrieve a selected one of the plurality of treatment options and for outputting the final Cobb angle prediction and the selected treatment option.

In some embodiments, the memory has stored thereon the predictive model comprising a general linear statistical model associating the final Cobb angle prediction with selected predictors, the selected predictors comprising the 3D morphological spine parameters, curve type, and skeletal maturity and determined by a backward selection procedure.

In accordance with another broad aspect, there is provided a computer-implemented method for generating a final Cobb angle prediction for idiopathic scoliosis, the method comprising receiving patient-specific 3D morphological spine parameters, a selected curve type, and a selected skeletal maturity; applying the patient-specific 3D morphological spine parameters, a selected curve type, and a selected skeletal maturity to a predictive model based on 3D morphological spine parameters, curve type, and skeletal maturity, and generating the final Cobb angle prediction by modeling a progression curve of the idiopathic scoliosis.

In some embodiments, the method further comprises receiving two-dimensional spine data, reconstructing a three-dimensional spine morphology, and extracting the patient-specific 3D morphological spine parameters therefrom.

In some embodiments, receiving the patient-specific 3D morphological spine parameters comprises receiving at least one of an initial Cobb angle, a plane of maximal deformation, a three-dimensional wedging of vertebral body and disk, an axial intervertebral rotation of an apex, upper and lower junctional level and thoracolumbar level, slenderness, and torsion.

In some embodiments, receiving the patient-specific 3D morphological spine parameters comprises receiving the initial Cobb angle computed in at least one of a frontal plane of the reconstructed three-dimensional spine morphology, a sagittal plane of the reconstructed three-dimensional spine morphology, and the plane of maximal deformation.

In some embodiments, receiving the patient-specific 3D morphological spine parameters comprises receiving the plane of maximal deformation as a plane in the reconstructed three-dimensional spine morphology having an axial angle that extends around a direction in which the initial Cobb angle is maximal.

In some embodiments, receiving the patient-specific 3D spine parameters comprises receiving three-dimensional wedging of junctional and peri-apical disk levels of the reconstructed three-dimensional spine morphology and a sum of three-dimensional wedging of all thoracic and lumbar disks of the reconstructed three-dimensional spine morphology.

In some embodiments, receiving the patient-specific 3D morphological spine parameters comprises receiving the axial intervertebral rotation computed for a superior vertebra of the reconstructed three-dimensional spine morphology relative to an inferior vertebra of the reconstructed three-dimensional spine morphology, the inferior vertebra adjacent the superior vertebra and the superior and inferior vertebrae each having defined therefor in the reconstructed three-dimensional spine morphology a local axis plane comprising a first axis, the rotation computed by projecting the first axis of the superior vertebra onto the local axis plane of the inferior vertebra.

In some embodiments, receiving the patient-specific 3D morphological spine parameters comprises receiving the slenderness computed as a ratio of a height to a width of a body of each one of thoracic and lumbar vertebrae of the reconstructed three-dimensional spine morphology.

In some embodiments, receiving the patient-specific 3D morphological spine parameters comprises receiving the torsion obtained by computing a first sum of the axial intervertebral rotation for all vertebrae in a first hemicurvature of a main idiopathic scoliosis curve in the reconstructed three-dimensional spine morphology, a second sum of the axial intervertebral rotation for all vertebrae in a second hemicurvature of the main curve, and a mean of the first sum and the second sum, the first hemicurvature defined between an upper end vertebra and an apex of the main curve and the second hemicurvature defined between a lower end vertebra of the main curve and the apex.

In some embodiments, the method further comprises querying a memory with at least one of the generated final Cobb angle prediction and the modelled progression curve to retrieve a selected one of a plurality of treatment options stored in the memory, each of the plurality of treatment options suitable for treating the idiopathic scoliosis and having associated therewith at least one of a range of final Cobb angles and a rate of change of idiopathic scoliosis curve progression, and outputting the final Cobb angle prediction and the selected treatment option.

In accordance with yet another broad aspect, there is provided a computer readable medium having stored thereon program code executable by a processor generating a final Cobb angle prediction for idiopathic scoliosis, the program code executable for receiving patient-specific 3D morphological spine parameters, a selected curve type, and a selected skeletal maturity; applying the patient-specific 3D morphological spine parameters, a selected curve type, and a selected skeletal maturity to a predictive model based on 3D morphological spine parameters, curve type, and skeletal maturity, and generating the final Cobb angle prediction by modeling a progression curve of the idiopathic scoliosis.

This technique of predicting scoliosis curve progression may help monitor patients with AIS and help tailor their treatment plan accordingly.

For the present specification, "Cobb angle" refers to a measure of the curvature of the spine, determined from measurements made on X-ray photographs. Specifically, scoliosis is defined by the Cobb angle. The Cobb angle is illustratively computed as the angle formed between a line drawn parallel (or perpendicular) to the superior endplate of the uppermost vertebra involved in the AIS deformity a line drawn parallel (or perpendicular) to the inferior endplate of the lowermost vertebra involved. A lateral and rotational spinal curvature of the spine with a Cobb angle of >10° is defined as scoliosis. "Risser sign" refers to a measurement of skeletal maturity. Skeletal maturity can be divided into three sequential stages: 1) Risser 0 with open triradiate cartilage, 2) Risser 0 with closed triradiate cartilage or Risser 1, and 3) Risser 2 or greater. The second stage correlates with the rapid acceleration phase. More precisely, a Risser sign is defined by the amount of calcification present in the iliac apophysis, divided into quartiles, and measures the progressive ossification from anterolaterally to posteromedially. A Risser grade of 1 signifies up to 25 percent ossification of the iliac apophysis, proceeding to grade 4, which signifies 100 percent ossification. A Risser grade of 5 means the iliac apophysis has fused to the iliac crest after 100 percent ossification. Children usually progress from a Risser grade 1 to a grade 5 over a two-year period during the most rapid skeletal growth.

Many other uses and advantages of the present invention will be apparent to those skilled in the art upon review of the detailed description herein. Solely for clarity of discussion, the invention is described in the sections below by way of non-limiting examples.

DETAILED DESCRIPTION

There is described a method and system for predicting final Cobb angle in idiopathic scoliosis based on information available at a first visit. In one embodiment, the method and system apply to AIS, as described herein. It should however be understood that other types of scoliosis, such as early onset idiopathic scoliosis, may also apply. A plane of maximal curvature is provided as a risk factor of progression. One or more of the following predictive factors are combined in order to obtain the predictive model: type of curvature, skeletal maturity, initial Cobb angle, angle of plane of maximal curvature, 3D wedging of junctional and peri-apical disks (e.g. T3-T4, T8-T9, T11-T12 disks) and sum of thoracic and lumbar 3D disks wedging.

Classical risk factors such as skeletal maturity, initial Cobb angle and type of curvature are found to predict final Cobb angle to a certain extent. The addition of the plane of maximal curvature as well as the sum of the disk wedging of the thoracic and lumbar levels and three specific 3D junctional and peri-apical disks wedging levels (e.g. T3-T4, T8-T9, T11-T12) improves the overall prediction of the final Cobb angle.

A study was performed with the objective of developing a predictive model of the final Cobb angle in adolescent idiopathic scoliosis based on 3D spine parameters. A prospective cohort was recruited in a single center from January 2006 to May 2010. The inclusion criteria were (1) first visit with an orthopedic surgeon with a diagnosis of AIS, (2) Cobb angle between 11 and 40 degrees, and (3) Risser sign of 0 or 1. The exclusion criteria were (1) congenital, neuromuscular or syndromic scoliosis. Patients with a Risser sign of 2 or greater were also excluded. Curves greater than 40 degrees were also excluded because they fall into a category in which some surgeons will consider a fusion surgery.

At the first and for all subsequent visits, each patient had a lateral and PA spine radiographs. Patients were followed by one of four (4) spine surgeons with intervals of follow up chosen by treating surgeon. The endpoint for the study occurred when patients reached skeletal maturity (at least Risser 4) or when a fusion surgery was performed. Brace treatment was allowed according to the treating physician, but brace had to be removed the night before appointment.

For all patients, the curve type was defined either as a single right thoracic, double with main thoracic, double with main lumbar, triple, single left thoracolumbar, single left lumbar or other (left thoracic and right lumbar). The Risser sign and triradiate cartilage status (open or closed) was evaluated at the first visit. The skeletal maturity status was set as either stage 0 (open triradiate cartilage and Risser 0) or stage 1 (Risser 0 with closed triradiate cartilage or Risser 1).

All patients had a 3D spinal reconstruction of the spine at the first visit from the PA and lateral radiographs. Reconstructions were done with two softwares: Spine 3D (LIS3D, Montreal, Canada) and IdefX (LIO, Montreal, Canada), by one research assistant expert in the technique. Two different softwares were used in order to conform with the specifications proper to each of the two radiographic imaging systems used in the current study: Spine 3D was used with the Fuji system (58 first patients of the cohort) and IdefX was used with the EOS™ system (75 last patients of the cohort). The Spine 3D software uses algorithms based on direct linear transformation combined with the Non Stereo Corresponding Points algorithm (NSCP); this is based on identification of corresponding anatomical landmarks on vertebrae from stereo-radiographs. IdefX software uses a semi-automated (SA) method based on a priori knowledge. Both softwares generated 3D reconstructions of comparable accuracy. There is no difference in terms of mean errors between 3D vertebral models obtained from stereo-radiography (NSCP and SA) and CT-scan reconstructions. The precision of these reconstructions has been shown to be very satisfactory with mean point-to-surface errors of less than 1.5 mm and less than two degrees for angular measurements when compared to conventional CT-Scan reconstructions.

All measurements were computerized 3D radiologic measurements done with the same custom software IdefX (LIO, Montreal, Canada) for all reconstructions.

The calculated 3D parameters were illustratively divided in six (6) categories consisting of global (whole spine), regional (scoliotic segment) or local (vertebra) descriptors. The centroid of each vertebra is defined as the point halfway between the center of the upper and lower endplates of the vertebra. The global axis system is defined by the SRS 3D terminology group as follows: the origin is at the center of the upper endplate of S1, the <<z>> axis is vertical (gravity line) and the <<y>> axis is between the anterior superior iliac spine and pointing to the left. The local vertebra axis system is defined by the SRS 3D terminology group as follows: the origin is at the centroid of the vertebral body, the local 'z' axis passes through the centers of the upper and lower endplates and pointing in a cephalad direction, and 'y' axis is parallel to a line joining similar landmarks on the bases of the right and left pedicles pointing to the left. An exemplary set of the 3D parameters for each parameter category is as follows. It should be understood that each parameter category may comprise several 3D parameters.

1—Cobb Angles: Cobb angles were defined as the angle between the upper and lower end plate of the respective end vertebrae of a curve. Cobb angle was measured in the frontal plane, in the plane of maximal deformation in 3D and in the sagittal plane for thoracic kyphosis (T4-T12) and lumbar lordosis (L1-L5).

Figure 1:
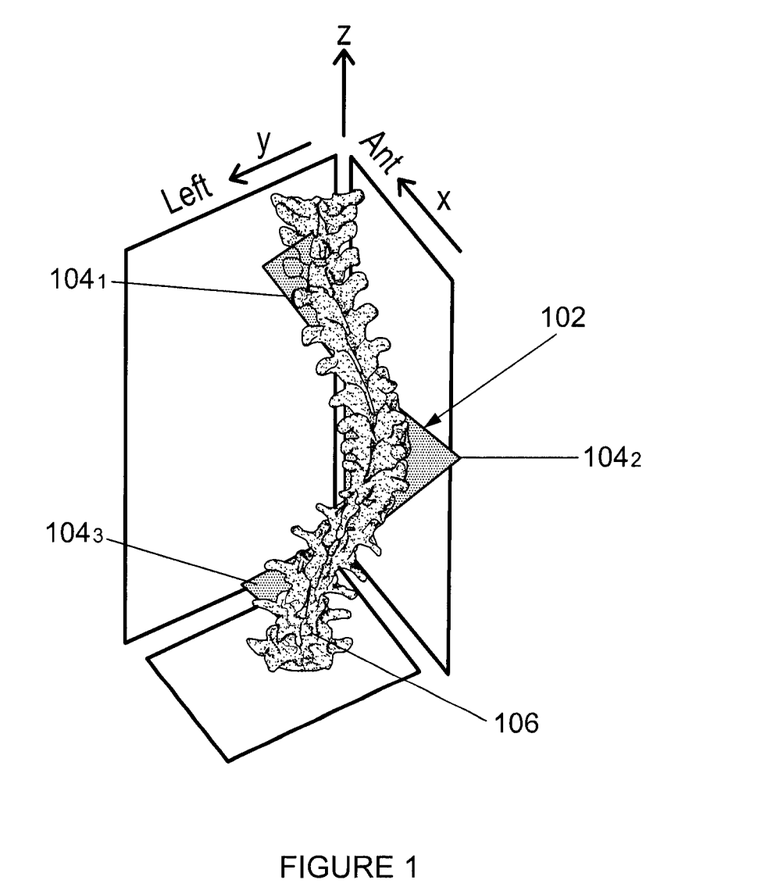
FIG. 1 illustrates a 3D reconstruction of a scoliotic spine with plane of maximal deformity represented by a triangle for each curvature (thoracic proximal curve, main thoracic and lumbar) in the axis system with <<x>> axis anterior, <<y>> axis left and <<z>> axis cephalad.

2—Plane of maximal deformation: Referring now to FIG. 1, there is illustrated a plane 102 of maximal deformation. The axial angle (not shown) of the plane 102 is around a direction, e.g. a global z-axis, in which the Cobb angle is maximal. The plane 102 of maximal deformation is illustratively represented by a triangle $104_1$, $104_2$, $104_3$ for each curvature in the spine 106, e.g. for the thoracic proximal curve, main thoracic curvature, and lumbar curvature, respectively.

Figure 2A:
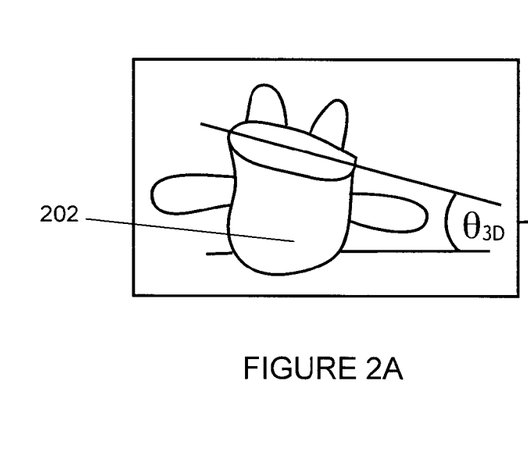
FIG. 2A illustrates the Vertebral body 3D wedging.
Figure 2B:
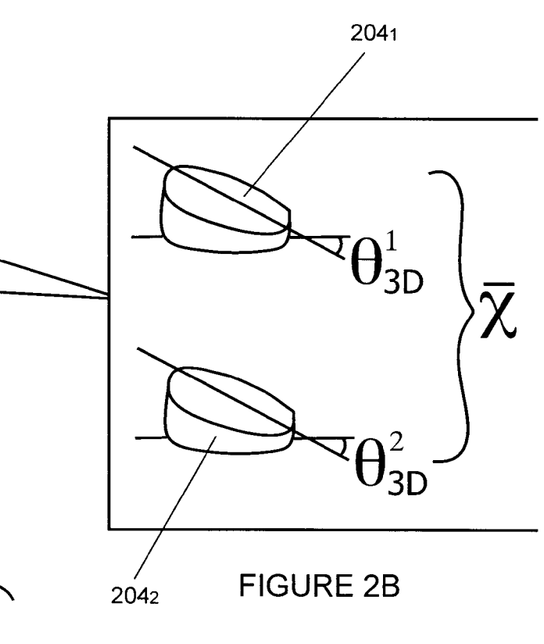
FIG. 2B is an illustration of the mean of the two apical 3D disks wedging.

3—Three-dimensional wedging of vertebral body and disk: FIGS. 2a and 2b illustrate three-dimensional wedging $\theta_{3D}$ of vertebral body and disk. Wedging of the apical vertebral body 202 in the plane 102 of maximal deformation (3D plane) and mean maximal 3D wedging of the two apical intervertebral disks as in $204_1$, $204_2$ are shown. Maximal 3D wedging represents the wedging measured in the plane, wherein the wedging value is maximal around the vertical axis. If the apex was a disk (see FIG. 2b), then the mean of the 3D wedging $\theta^1_{3D}$, $\theta^2_{3D}$ of both apical vertebral bodies was calculated and only the 3D wedging of the apical disk was reported instead of the mean of two apical disks. 3D disk wedging was analyzed for all levels of the thoracic and lumbar spine (from T1-T2 to L4-L5).

Figure 3A:
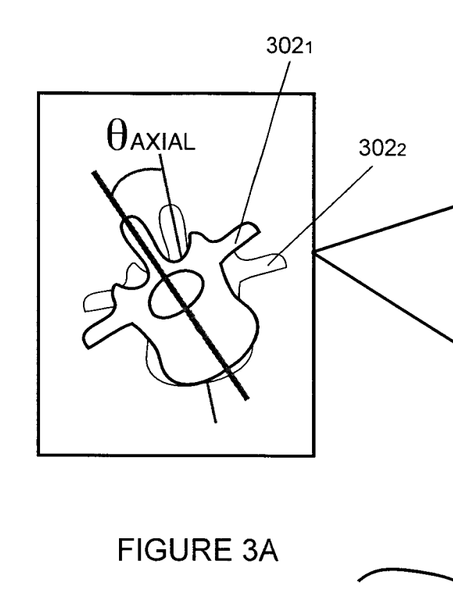
FIG. 3A is an illustration of intervertebral rotation.

4—Axial intervertebral rotation of the apex, upper and lower junctional level and thoracolumbar level: This is shown in FIG. 3a. In particular, rotation between two adjacent vertebrae $302_1$, $302_2$ at upper, apical and lower curve level and thoracolumbar junction (T12-L1) with reference to the local axis system of the inferior vertebra $302_2$ are illustrated. The rotation $\theta_{AXIAL}$ of the superior vertebra $302_1$ with respect to the inferior vertebra $302_2$ was calculated after projecting the local x-axis of the superior vertebra $302_1$ into the x-y plane of the local axis system of the inferior vertebra $302_2$. The definition of the SRS 3D terminology group for the intervertebral rotation is the projected angles between the local axis of two adjacent vertebrae.

Figure 3B:
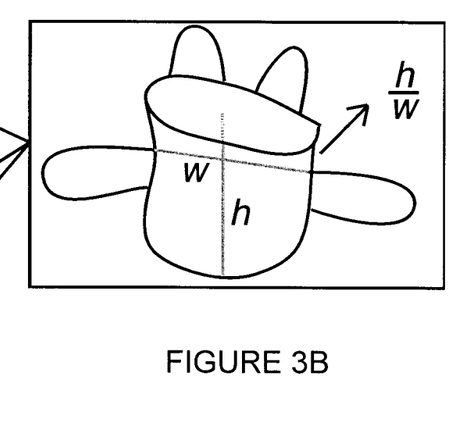
FIG. 3B in an illustration of slenderness with height/width (h/w) ratio of a single vertebral body.

5—Slenderness: FIG. 3b illustrates slenderness (local T6, T12 and L4 and regional T1-L5), or the ratio between the height h (distance between the superior and inferior end plates at the center of the vertebrae) and the width w (measured at the center of the vertebrae using a line perpendicular to the height line in medio-lateral direction) of the vertebral body for T6, T12 and L4 vertebrae. Ratio may also be found between the length of the spine between T1 and L5 and the mean of the width of vertebral bodies of T6, T12 and L4. The same calculations were made with the width being replaced by the depth (a line perpendicular to the height line at the center of the vertebra in the antero-posterior direction). The length between T1-L5 is the length of a line starting at the center of the upper endplate of T1, passing through the centroid of all vertebrae down to the center of the lower endplate of L5. The line was smoothed using a cubic spline function. T6 and L4 were selected and T12 was added as a thoracolumbar landmark. It should however be understood that slenderness calculation is not limited to T6, T12, and L4 vertebrae and may apply to any thoracic or lumbar vertebra.

Figure 4:
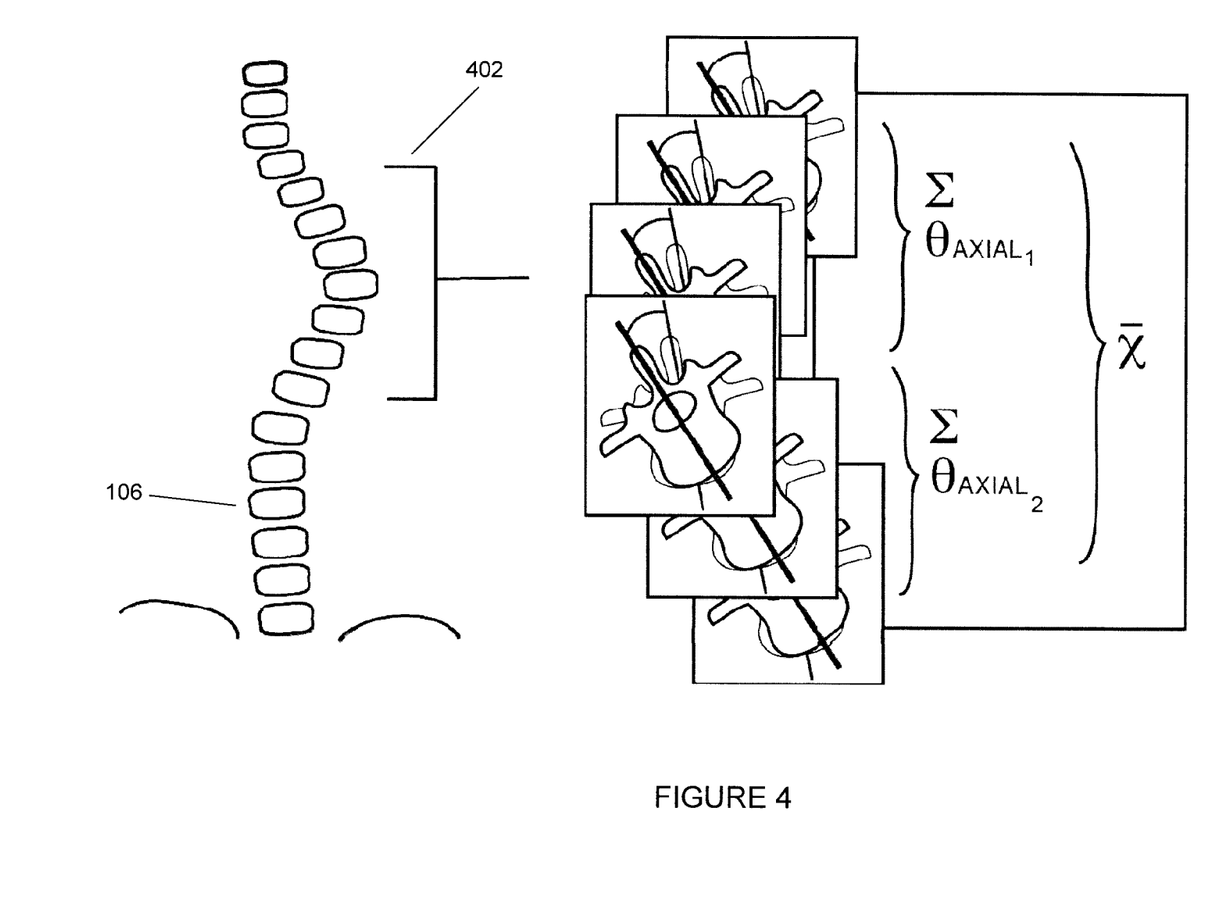
FIG. 4 is an illustration of torsion. $\chi$ (mean) $\Sigma$ (sum) $\theta$ (angle)

6—Torsion: FIG. 4 illustrates mechanical torsion, or the mean of the sum of intervertebral axial rotation (measured according to the local referential of the inferior vertebrae) for all vertebrae included in the two hemicurvatures (between upper end vertebra and apex and between lower end vertebra and apex, not shown) of the main scoliotic curve 402 of the spine 106. For this purpose, a first sum $\Sigma\theta_{AXIAL1}$ of intervertebral axial rotation for all vertebrae in the first hemicurvature (not shown) is computed. A second sum $\Sigma\theta_{AXIAL2}$ of intervertebral axial rotation for all vertebrae in the second hemicurvature (not shown) is further computed. The mean of the first and second sums $\Sigma\theta_{AXIAL1}$, $\Sigma\theta_{AXIAL2}$ is then computed to obtain the value of the torsion. As discussed above, geometrical torsion may also apply.

In a specific embodiment, the output of the prediction method was defined as the main Cobb angle measured on a posteroanterior (PA) radiograph at the earliest visit where skeletal maturity (minimum Risser 4) was reached or just before fusion surgery.

Figure 5:
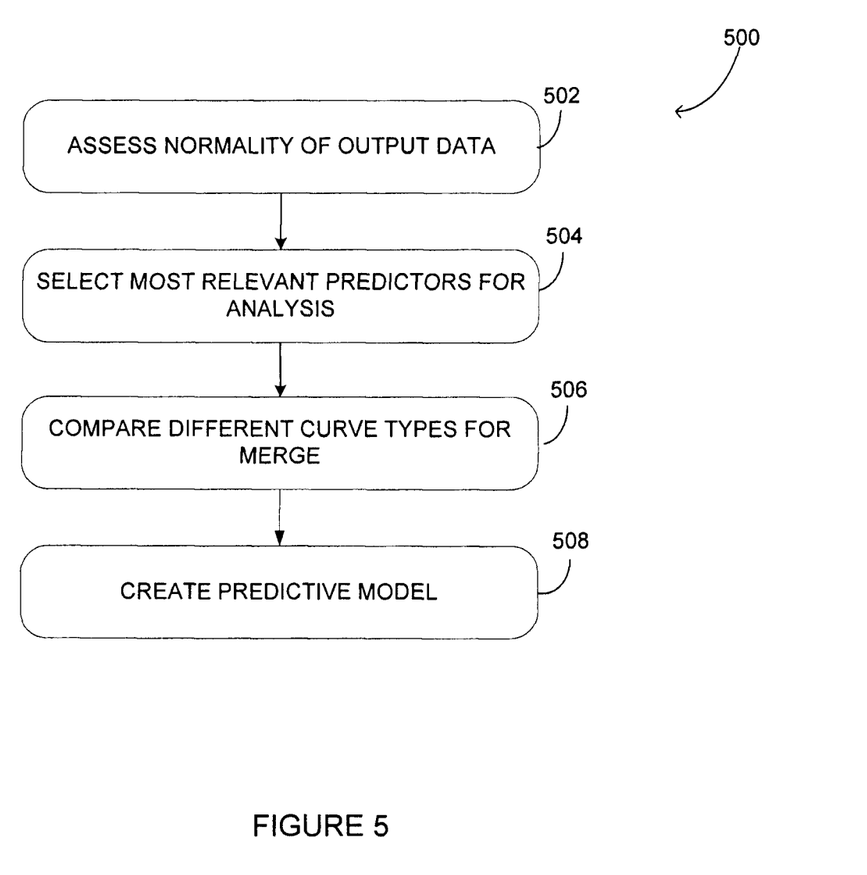
FIG. 5 is a flowchart of an exemplary method for creating a predictive model for AIS.

FIG. 5 is a flowchart of an exemplary method for generating the predictive model 500. The first step 502 was to assess the normality of the output data from a frequency histogram as well as from subjective analysis of the normal distribution.

Due to the large number of variables, the second step 504 was to do univariate analyses to select the most relevant predictors to be included in the multivariate analysis. Initially, the correlations between final Cobb angle at skeletal maturity and local, regional and global parameters of the spine can be performed in order to identify parameters associated with a p value of 0.1 or less.

The third step 506 was done to reduce the number of categories for the curve type. A one-way analysis of variance (ANOVA) can be done to compare the six different curve types in terms of final Cobb angle at skeletal maturity with a level of significance of 0.05, in order to merge curve types resulting in similar final Cobb angle at skeletal maturity. The objective of this step was to reduce the number of different categories for the type of curve input in the model.

The final step 508 consisted in creating the predictive model based on a General Linear Model (GLM). A backward selection procedure approach was performed to select predictors. P-values were first obtained for each predictor included in the full model (curve type and skeletal maturity stage were included as fixed factors and all retained spinal parameters were included as covariates). Interaction was added between categorical variable to test if a change in the simple main effect of one variable over the level of the second was significant.

The predictor with the larger p-value was then eliminated and the model was refitted. This was done until all remaining predictors were associated with a p-value smaller than the stopping criterion set at 0.05. In the GLM, association between the final Cobb angle at skeletal maturity and selected predictors was assessed and expressed as beta coefficient (β coefficient) and 95% confidence interval (CI).

All statistical analyses were done with SPSS 20.0 software package (SPSS, inc., Chicago, Ill., USA).

In one exemplary embodiment, a prospective cohort of 133 AIS was followed from skeletal immaturity to maturity (mean 37 months). A total of 172 AIS patients were entered in the cohort. At the time of the analysis, 133 patients could be included (77.3%). Overall, 17 were lost to follow up, 13 were still skeletally immature and 3D reconstruction was impossible for 9 patients due to calibration errors. Descriptive characteristics of the cohort are presented in table 1, using the following acronyms: n (sample size), TR (triradiate cartilage), RT (right thoracic), RT-LL (right thoracic-left lumbar), LL-RT (left lumbar-right thoracic), LTL (left thoracolumbar), other (left thoracic, right lumbar).

TABLE 1

| | | Cohort |
|---|---|---|
| N | | 133 |
| Age (years) | | 12.6 ± 1.2 |
| Sex | Male | 16 |
| | Female | 117 |
| Risser | 0 and TR open | 48 |
| | 0 and TR closed | 47 |
| | 1 | 38 |
| Cobb angle (degrees) | | 22.1 ± 8.4 |
| Follow up (month) | | 36.7 ± 13.6 |
| Type | RT | 35 |
| | RT-LL | 22 |
| | LL-RT | 26 |
| | Triple | 7 |

TABLE 1-continued

| | | Cohort |
|---|---|---|
| | LTL | 36 |
| | Other | 7 |
| Treatment | Observation | 51 |
| | Brace | 66 |
| | Fusion surgery | 16 |

Computerized measurements were done on reconstructed 3D spines radiographs of the first visit. There were six (6) categories of measurements or parameters, each category comprising several measurements or parameters: angle of plane of maximum curvature, Cobb angles (kyphosis, lordosis), 3D wedging (apical vertebra, apical disks), rotation (upper and lower junctional vertebra, apical vertebra, thoracolumbar junction), mean peri-apical intervertebral rotation (geometrical and/or mechanical torsion) and slenderness (height/width ratio). A general linear model analysis with backward procedure was done with final Cobb angle (either just before surgery or at skeletal maturity) as outcome and 3D spine parameters as predictors. Skeletal maturity stage and type of curvature were also included in the model.

In a specific embodiment, the predictive model was obtained with a determination coefficient of 0.715. Included predictors were a three (3) stages skeletal maturity system and type of curvature. The initial frontal Cobb angle was also included as well as the angle of the plane of maximal curvature. The four (4) other predictive factors of final Cobb angle were the 3D wedging of T3-T4, T8-T9 and T11-T12 disks, and the sum of 3D wedging of all thoracic and lumbar disks. As discussed above, it should be understood that, in other embodiments, 3D wedging of junctional and peri-apical disk levels other than T3-T4, T8-T9, and T11-T12 may apply.

Figure 6:
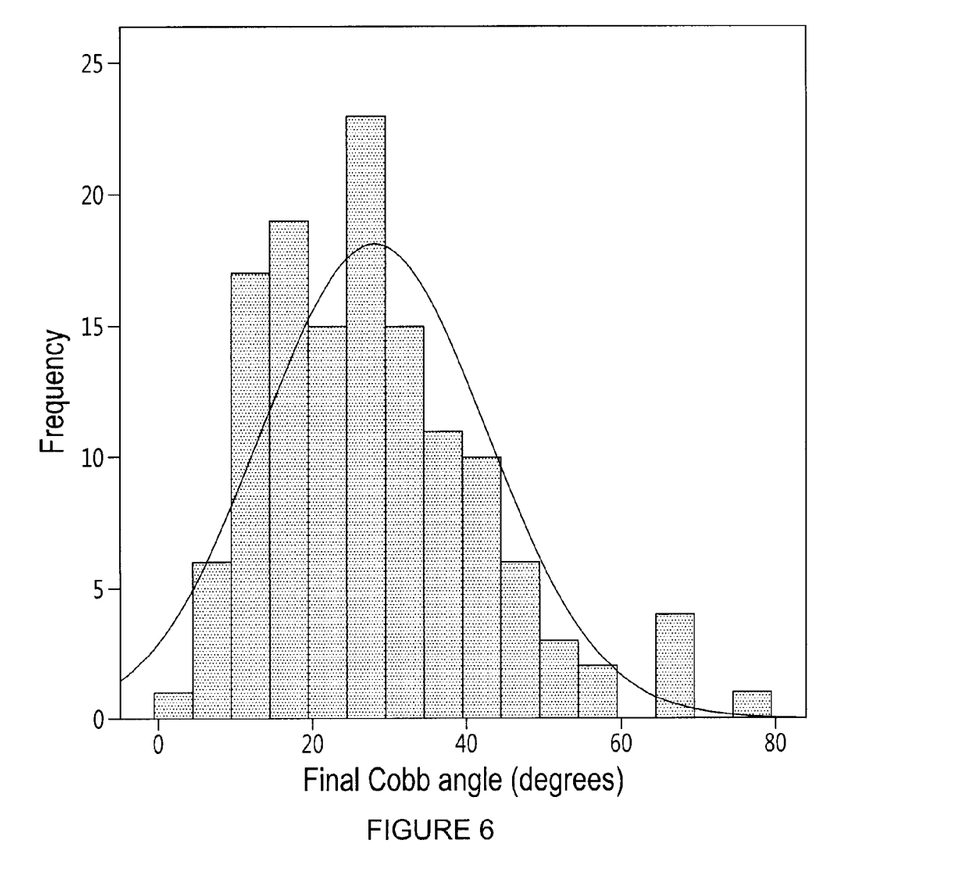
FIG. 6 represents the frequency histogram with final Cobb angle on <<x>> axis and frequency on <<y>> axis with a normal curve illustrated.

The final Cobb angle distribution followed a normal distribution, as shown by the histogram presented in FIG. 6.

Pearson's correlations with the final Cobb angle were done for a total of forty-one (41) spinal parameters. There were thirty (30) parameters resulting in a correlation associated with a p-value under 0.1. The results of the correlation analysis are illustrated in table 2.

TABLE 2

| Parameters | Pearson coefficient | P-value |
|---|---|---|
| 3D kyphosis (T4-T12) | −0.285 | 0.001 |
| Mean apical disks 3D wedging | 0.364 | 0.000 |
| Proximal disk 3D wedging | 0.23 | 0.007 |
| Distal disk 3D wedging | −0.174 | 0.043 |
| Distal IV rotation | −0.16 | 0.063 |
| Thoracolumbar IV rotation (T12-L1) | −0.159 | 0.071 |
| Apical IV rotation | −0.164 | 0.057 |
| Cobb angle in the plane of maximal deformation | 0.287 | 0.001 |
| Angle of the plane of maximal deformation | 0.501 | 0.000 |
| Torsion | 0.412 | 0.000 |
| Cobb angle frontal plane | 0.659 | 0.000 |
| T6 Slenderness (depth) | −0.169 | 0.050 |
| T6 Slenderness (width) | −0.183 | 0.034 |
| L4 Slenderness (depth) | −0.203 | 0.018 |
| L4 Slenderness (width) | −0.165 | 0.055 |
| T1-L5 Slenderness (width) | −0.226 | 0.008 |
| T1-L5 Slenderness (depth) | −0.198 | 0.021 |
| T1-T2 3D disk wedging | 0.379 | 0.000 |
| T2-T3 3D disk wedging | 0.268 | 0.002 |
| T3-T4 3D disk wedging | 0.386 | 0.000 |
| T5-T6 3D disk wedging | 0.182 | 0.034 |
| T6-T7 3D disk wedging | 0.192 | 0.025 |

TABLE 2-continued

| Parameters | Pearson coefficient | P-value |
|---|---|---|
| T7-T8 3D disk wedging | 0.33 | 0.000 |
| T8-T9 3D disk wedging | 0.466 | 0.000 |
| T9-T10 3D disk wedging | 0.314 | 0.000 |
| T10-T11 3D disk wedging | 0.341 | 0.000 |
| T11-T12 3D disk wedging | 0.249 | 0.004 |
| T12-L1 3D disk wedging | 0.305 | 0.000 |
| L1-L2 3D disk wedging | 0.184 | 0.033 |
| Sum of 3D disks wedging (Thoracic and lumbar) | 0.412 | 0.000 |

For the type of curvature, the ANOVA analysis reduced the six (6) categories into four (4) types which are (1) right thoracic, double with main left lumbar and other type (left thoracic, right lumbar), (2) triple, (3) left thoracolumbar, and (4) double with main right thoracic.

With regards to the GLM analysis, skeletal maturity, type of curve, 2D initial Cobb angle, angle of the plane of maximal deformation, disk wedging of T3-T4, T8-T9, T11-T12 and sum of lumbar and thoracic wedging were found to be predictors of the final Cobb angle. Table 3 illustrates the GLM ($R^2$=0.715, F=22.956, p<0.000) to determine predictors of final Cobb angle.

TABLE 3

| Parameters | | n | Estimated coefficient | 95% CI Upper | 95% CI Lower | p-value |
|---|---|---|---|---|---|---|
| Intercept | | 133 | 0.288 | −7.788 | 8.364 | 0.944 |
| Angle of plane of maximal curvature | | 133 | 0.177 | 0.097 | 0.256 | 0.000 |
| 2D Cobb angle | | 133 | 0.714 | 0.479 | 0.949 | 0.000 |
| T3-T4 disk wedging | | 133 | 1.185 | 0.456 | 1.914 | 0.002 |
| T8-T9 disk wedging | | 133 | 0.992 | 0.24 | 1.745 | 0.010 |
| T11-T12 disk wedging | | 133 | 0.868 | 0.133 | 1.603 | 0.021 |
| Sum of all thoracic and lumbar disk wedging | | 133 | −0.134 | −0.251 | −0.016 | 0.026 |
| Maturity | 0 | 48 | 8.7 | 1.041 | 16.359 | 0.026 |
| | 1 | 85 | $0^b$ | | | |
| Type of curvature | 1 | 68 | −4.566 | −9.599 | 0.466 | 0.075 |
| | 2 | 7 | 3.959 | −8.637 | 16.556 | 0.535 |
| | 3 | 36 | −3.201 | −8.728 | 2.326 | 0.254 |
| | 4 | 22 | $0^b$ | | | |

| Interaction Type | Maturity | | | | | |
|---|---|---|---|---|---|---|
| 1 | 0 | 26 | −2.868 | −11.454 | 5.718 | 0.510 |
| 1 | 1 | 42 | $0^b$ | | | |
| 2 | 0 | 5 | 8.969 | −6.854 | 24.793 | 0.264 |
| 2 | 1 | 2 | $0^b$ | | | |
| 3 | 0 | 10 | −14.56 | −24.276 | −4.843 | 0.004 |
| 3 | 1 | 26 | $0^b$ | | | |
| 4 | 0 | 7 | $0^b$ | | | |
| 4 | 1 | 15 | $0^b$ | | | |

All continuous predictors increased the final value of Cobb angle except the sum of disk wedging for which the β coefficient is negative (−0.134). The initial Cobb angle has a coefficient of 0.714. If the patient has a skeletal maturity stage of 0, 8.7° are added to the final Cobb angle prediction when compared to a similar patient with skeletal maturity stage 1. For the type of curvature, 4.6° (type 1) or 3.2° (type 3) are subtracted to the final Cobb angle, or 4.0° is added for type 2, when compared to a similar patient with a type 4 curve. This is adjusted with the interaction contribution. A type 1 with 0 as maturity stage will have 2.9° subtracted, a type 2 with 0 as maturity stage will have 9.0° added and type 3 with 0 as maturity stage will have 14.6° subtracted to the final Cobb angle prediction. R2 of this predictive model is 0.715, which means that it explains 71.5% of variance.

Some p-values for the categorical predictors are over 0.05 when evaluating their main effect in the GLM. However, these categorical predictors were kept in the model because their contribution was significant when considered in interaction between each other.

Predictors of progression were identified for immature patients with AIS that will facilitate the prediction of progression until skeletal maturity in mild and moderate curves with a Cobb angle between 11° and 40°. The prediction model can explain 71.5% of the variance in the final Cobb angle at skeletal maturity using only information taken from the initial visit.

Basics predictors included in the model are the Cobb angle, type of curvature and skeletal maturity at the initial visit.

One 3D parameter comprised in the model is the angle of the plane of maximal deformation. This parameter is associated with the rotation of the curve and may be more sensitive to detect progressive AIS than traditional Cobb angle.

The four (4) other predictors comprised in the model are disc wedging (at junctional and peri-apical disk levels, e.g. T3-T4, T8-T9, T11-T12, and sum of all). T3-T4 and T11-T12 levels that were identified usually represent junctional level and T8-T9 either junctional or apical level depending on the type of curvature (for a thoracic curve it will represent apical level and for thoracolumbar curve, junctional level). Wedging of T3-T4 disks has the largest effect on final Cobb angle prediction.

The statistical model chosen was a GLM with a backward procedure to select the predictors. A stepwise selection variant is widely used in medical application and it was chosen because it represents a good strategy to find the best fitting model. It is accepted that a sample size of more than a hundred (100) is required for linear modeling. Another way to determine the sample size of linear modeling is to have at least ten (10) times the degree of freedom included in model. This model has thirteen (13) degrees of freedom (six (6) continuous predictors, one (1) for maturity stage, three (3) for curve type and three (3) for the combination of maturity stage and type of curvature), so the sample size of one hundred and thirty three (133) is suitable.

Figure 7:
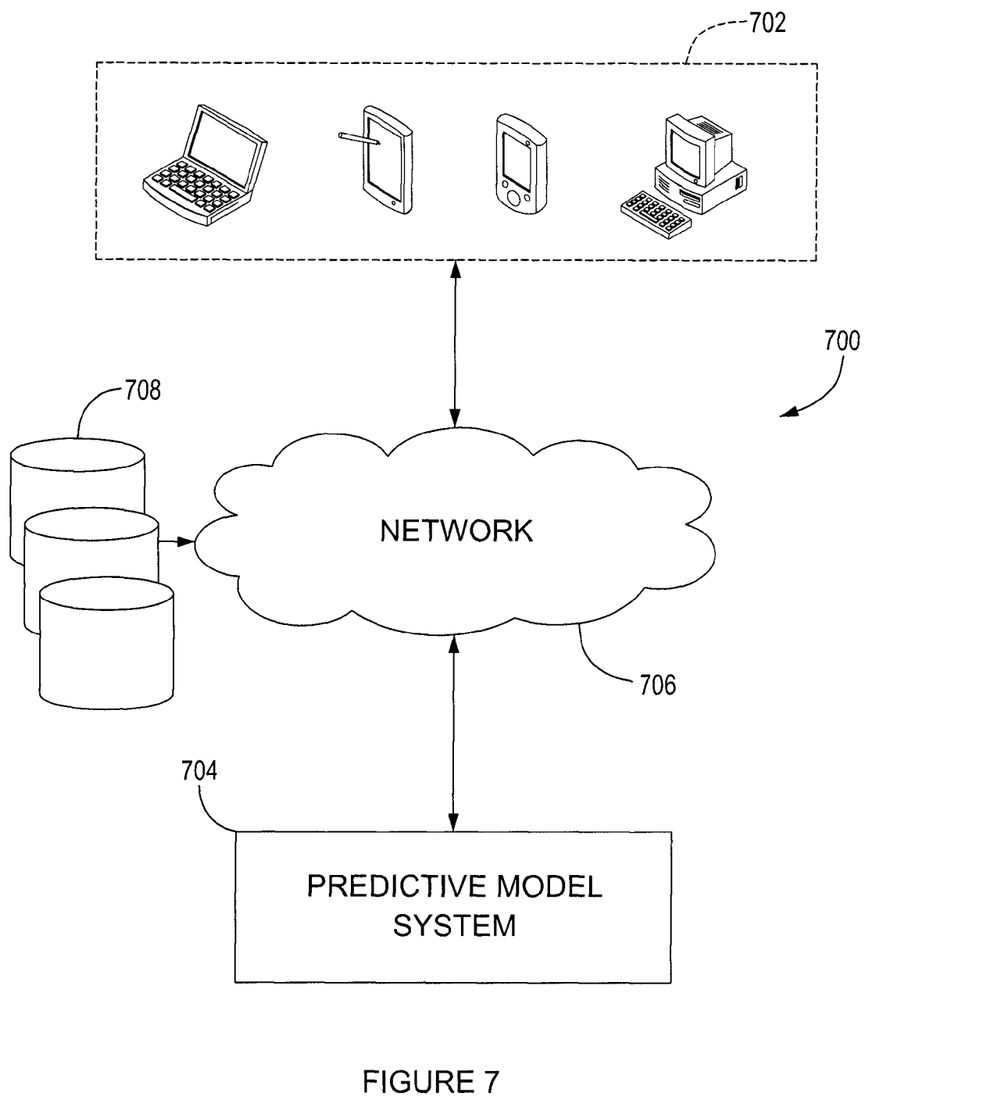
FIG. 7 is a block diagram of an exemplary system for predictive modeling of AIS.

Referring to FIG. 7, a communication system 700 for providing health care providers with support in predicting a curve of progression for AIS will now be described. The system 700 comprises a plurality of devices as in 702 adapted to communicate with a predictive model system 704 over a network 706. The devices 702 comprise any device, such as a personal computer, a personal digital assistant, a smart phone, or the like, which is configured to communicate over the network 706, such as the Internet, the Public Switch Telephone Network (PSTN), a cellular network, or others known to those skilled in the art. Although illustrated as being separate and remote from the devices 702, it should be understood that the predictive model system 704 may also be integrated with the devices 702, either as a downloaded software application, a firmware application, or a combination thereof.

One or more databases 708 may be integrated directly into the predictive model system 704 or may be provided separately and/or remotely therefrom, as illustrated. In the case of a remote access to the databases 708, access may occur via any type of network 706, as indicated above. The databases 708 may be provided as collections of data or information organized for rapid search and retrieval by a computer. The databases 708 may be structured to facilitate storage, retrieval, modification, and deletion of data in conjunction with various data-processing operations. The databases 708 may consist of a file or sets of files that can be broken down into records, each of which consists of one or more fields. Database information may be retrieved through queries using keywords and sorting commands, in order to rapidly search, rearrange, group, and select the field. The databases 708 may be any organization of data on a data storage medium, such as one or more servers.

In one embodiment, the databases 708 are secure web servers and Hypertext Transport Protocol Secure (HTTPS) capable of supporting Transport Layer Security (TLS), which is a protocol used for access to the data. Communications to and from the secure web servers may be secured using Secure Sockets Layer (SSL). Identity verification of a user may be performed using usernames and passwords for all users. Various levels of access rights may be provided to multiple levels of users.

Alternatively, any known communication protocols that enable devices within a computer network to exchange information may be used. Examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), SSH (Secure Shell Remote Protocol).

Figure 8:
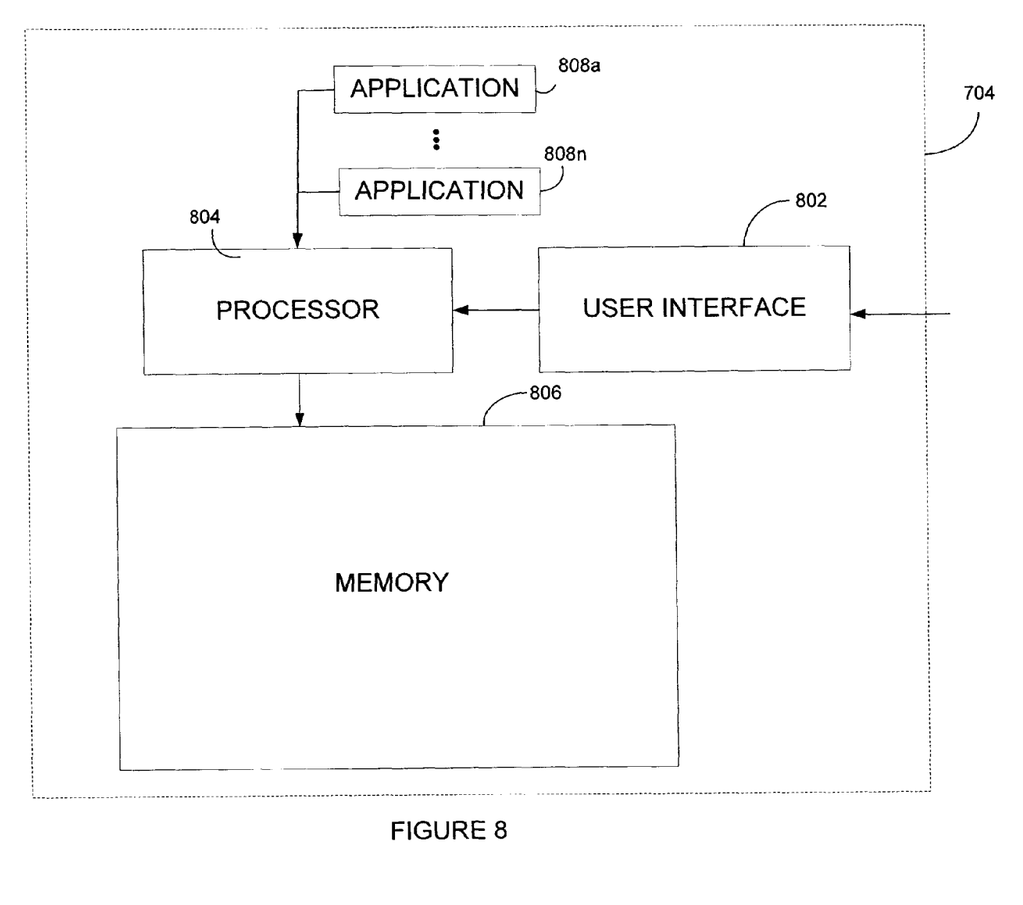
FIG. 8 is a block diagram of an exemplary system for the predictive model system of FIG. 7.

Referring now to FIG. 8, the predictive model system 704 illustratively comprises a user interface 802 through which the user may interact with the predictive model system 704. In particular and as will be discussed in further detail herein below, the user (e.g. a physician) may use the user interface 802 to submit information to the predictive model system 704. As indicated above, the information may be obtained during the first visit, and comprise basis predictors, such as Cobb angle, type of curvature, and skeletal maturity, as well s 3D morphologic parameters. The user interface 802 may be used to access the information from a memory 806 located locally or remotely from the predictive model system 704.

The predictive model system 704 further comprises a processor 804, which may be any device that can perform operations on data. Examples are a central processing unit (CPU), a front-end processor, a microprocessor, a graphics processing unit (GPUNPU), a physics processing unit (PPU), a digital signal processor, and a network processor. A plurality of applications 808a . . . 808n are illustratively running on the processor 804 for performing operations required at the processor 804 in order to output a predicted final Cobb angle based on the information entered via the user interface 802. It should be understood that while the applications 808a . . . 808n presented herein are illustrated and described as separate entities, they may be combined or separated in a variety of ways.

The processor 804 is in communication with memory 806 which may receive and store data. The memory 806 may be a main memory, such as a high speed Random Access Memory (RAM), or an auxiliary storage unit, such as a hard disk or flash memory. The memory 806 may be any other type of memory, such as a Read-Only Memory (ROM), Erasable Programmable Read-Only Memory (EPROM), or optical storage media such as a videodisc and a compact disc.

Figure 9:
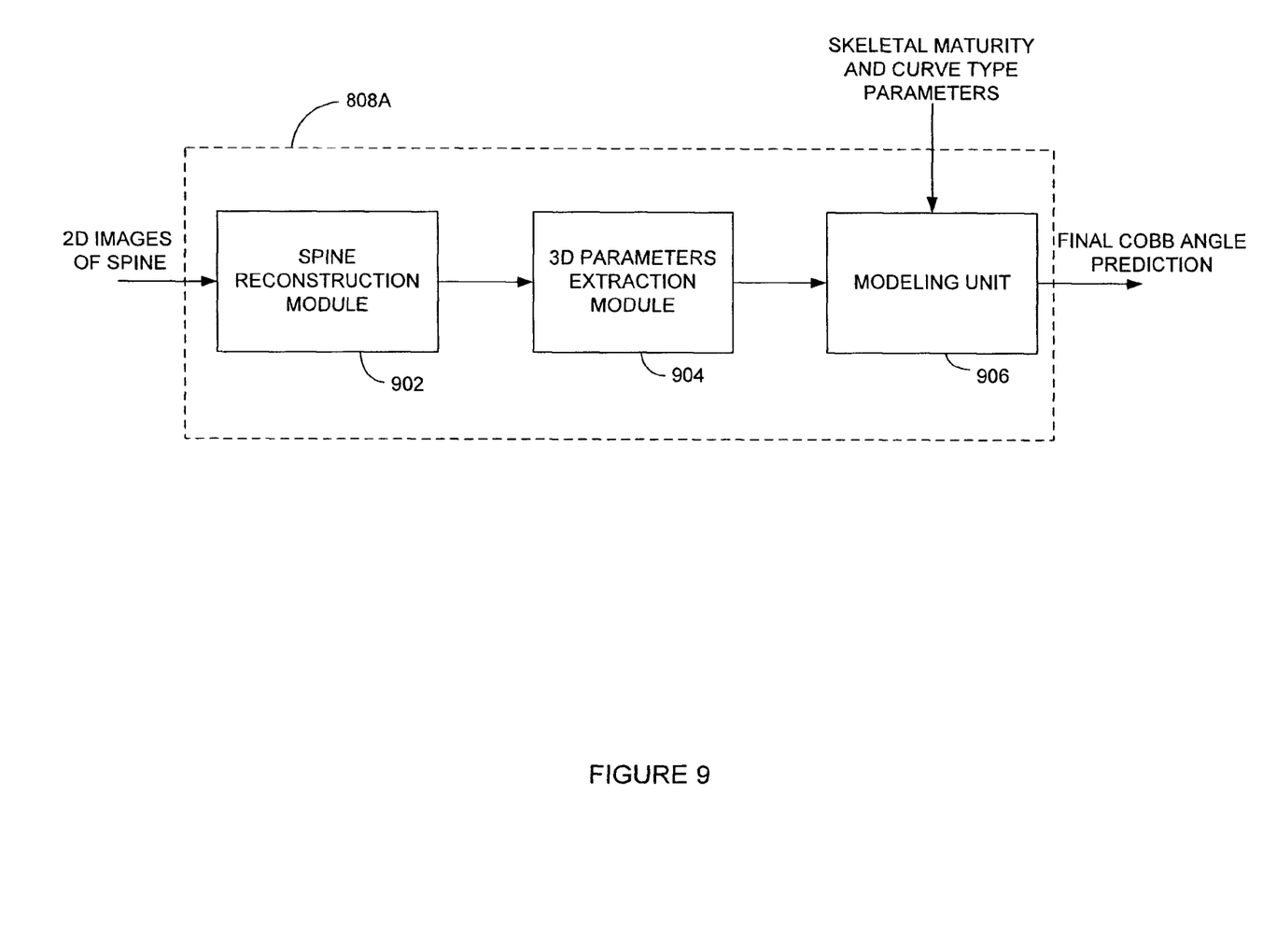
FIG. 9 is a block diagram of an exemplary application running on the predictive model system of FIG. 8.

FIG. 9 illustratively represents application 808a for generating a final Cobb angle prediction. Two-dimensional images of the spine, such as those obtained from radiographic imaging systems or other imaging systems, are provided to a spine reconstruction module 902. Three-dimensional morphology of the spine is thus provided and a 3D parameters extraction module 904 is configured to receive the 3D data and extract therefrom parameters such as the initial Cobb angle, the plane of maximal deformation, the three-dimensional wedging of vertebral body and disk, the axial intervertebral rotation of the apex, upper and lower junctional level and thoracolumbar level, slenderness, and torsion. These parameters are provided to a modeling unit 906 and combined with the skeletal maturity and curve type parameters to model the progression curve of AIS and output a final Cobb angle prediction value. The output of the predictive model system 704 is an aid to the treating physician to determine if the risk of progression warrants additional treatment.

In some embodiments, the predictive model system 704 is further adapted to sketch the curve of progression using the initial Cobb angle and the final Cobb angle. This curve may be output to the user via the user interface 802 or another output device, such as a printer. In some embodiments, the predictive model system 704 is also adapted to select from a series of recommended treatment options as a function of the final Cobb angle and/or the curve of progression generated using the initial and final Cobb angles. The treatment options may be categorized as a function of ranges of final Cobb angles and/or rates of change of the curve of progression such that selection is made of a most appropriate recommended treatment. The selected treatment(s) may then be output to the devices 702 for rendering thereon via the user interface 802 or other output device. Other embodiments for assisting the treating physician with treatment options once the final Cobb angle prediction has been generated will be readily understood by those skilled in the art.

While illustrated in the block diagrams as groups of discrete components communicating with each other via distinct data signal connections, it will be understood by those skilled in the art that the present embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiment. It should be noted that the present invention can be carried out as a method, can be embodied in a system, or on a computer readable medium. The embodiments of the invention described above are intended to be exemplary only. The scope of the invention is therefore intended to be limited solely by the scope of the appended claims.

The invention claimed is:

1. A system for generating a final Cobb angle prediction for idiopathic scoliosis, the system comprising:
    a memory having stored thereon a predictive model based on 3D morphological spine parameters, curve type, and skeletal maturity;
    a processor; and
    at least one application stored in the memory and executable by the processor for:
        receiving patient-specific data comprising 3D morphological spine parameters, a selected curve type, and a selected skeletal maturity;
        retrieving the predictive model;

modeling a progression curve of the idiopathic scoliosis using the patient-specific data and the predictive model; and generating a prediction of the final Cobb angle from the progression curve.

2. The system of claim 1, wherein the at least one application is further configured to receive two-dimensional spine data, reconstruct a three-dimensional spine morphology, and extract the patient-specific 3D morphological spine parameters therefrom, the patient-specific 3D morphological spine parameters comprising at least one of an initial Cobb angle, a plane of maximal deformation, a three-dimensional wedging of vertebral body and disk, an axial intervertebral rotation of an apex, upper and lower junctional level and thoracolumbar level, slenderness, and torsion.

3. The system of claim 2, wherein the at least one application is executable by the processor for computing the initial Cobb angle in at least one of a frontal plane of the reconstructed three-dimensional spine morphology, a sagittal plane of the reconstructed three-dimensional spine morphology, and the plane of maximal deformation.

4. The system of claim 2, wherein the at least one application is executable by the processor for computing the plane of maximal deformation as a plane in the reconstructed three-dimensional spine morphology having an axial angle that extends around a direction in which the initial Cobb angle is maximal.

5. The system of claim 2, wherein the at least one application is executable by the processor for computing three-dimensional wedging of junctional and peri-apical disk levels of the reconstructed three-dimensional spine morphology and a sum of three-dimensional wedging of all thoracic and lumbar disks of the reconstructed three-dimensional spine morphology.

6. The system of claim 2, wherein the at least one application is executable by the processor for computing the axial intervertebral rotation of a superior vertebra of the reconstructed three-dimensional spine morphology relative to an inferior vertebra of the reconstructed three-dimensional spine morphology, the inferior vertebra adjacent the superior vertebra and the superior and inferior vertebrae each having defined therefor in the reconstructed three-dimensional spine morphology a local axis plane comprising a first axis, the rotation computed by projecting the first axis of the superior vertebra onto the local axis plane of the inferior vertebra.

7. The system of claim 2, wherein the at least one application is executable by the processor for computing the slenderness as a ratio of a height to a width of a body of each one of thoracic and lumbar vertebrae of the reconstructed three-dimensional spine morphology.

8. The system of claim 2, wherein the at least one application is executable by the processor for receiving the patient-specific 3D morphological spine parameters comprising at least one of a mechanical torsion and a geometrical torsion, the mechanical torsion obtained by computing a first sum of the axial intervertebral rotation for all vertebrae in a first hemicurvature of a main idiopathic scoliosis curve in the reconstructed three-dimensional spine morphology, a second sum of the axial intervertebral rotation for all vertebrae in a second hemicurvature of the main curve, and a mean of the first sum and the second sum, the first hemicurvature defined between an upper end vertebra and an apex of the main curve and the second hemicurvature defined between a lower end vertebra of the main curve and the apex.

9. The system of claim 1, wherein the memory has stored therein a plurality of treatment options each suitable for treating the idiopathic scoliosis and having associated therewith at least one of a range of final Cobb angles and a rate of change of idiopathic scoliosis curve progression, and further wherein the at least one application is executable by the processor for querying the memory with at least one of the final Cobb angle prediction and the modelled progression curve to retrieve a selected one of the plurality of treatment options and for outputting the final Cobb angle prediction and the selected treatment option.

10. The system of claim 1, wherein the memory has stored thereon the predictive model comprising a general linear statistical model associating the final Cobb angle prediction with selected predictors, the selected predictors comprising the 3D morphological spine parameters, curve type, and skeletal maturity and determined by a backward selection procedure.

11. A computer-implemented method for generating a final Cobb angle prediction for idiopathic scoliosis, the method comprising:

receiving patient-specific data comprising 3D morphological spine parameters, a selected curve type, and a selected skeletal maturity;

applying the patient-specific 3D morphological spine parameters, a selected curve type, and a selected skeletal maturity to a predictive model based on 3D morphological spine parameters, curve type, and skeletal maturity;

modeling a progression curve of the idiopathic scoliosis from the predictive model; and generating a prediction of the final Cobb angle from the progression curve.

12. The method of claim 11, further comprising receiving two-dimensional spine data, reconstructing a three-dimensional spine morphology, and extracting the patient-specific 3D morphological spine parameters therefrom, the patient-specific 3D morphological spine parameters comprising at least one of an initial Cobb angle, a plane of maximal deformation, a three-dimensional wedging of vertebral body and disk, an axial intervertebral rotation of an apex, upper and lower junctional level and thoracolumbar level, slenderness, and torsion.

13. The method of claim 12, wherein receiving the patient-specific 3D morphological spine parameters comprises receiving the initial Cobb angle computed in at least one of a frontal plane of the reconstructed three-dimensional spine morphology, a sagittal plane of the reconstructed three-dimensional spine morphology, and the plane of maximal deformation.

14. The method of claim 12, wherein receiving the patient-specific 3D morphological spine parameters comprises receiving the plane of maximal deformation as a plane in the reconstructed three-dimensional spine morphology having an axial angle that extends around a direction in which the initial Cobb angle is maximal.

15. The method of claim 12, wherein receiving the patient-specific 3D spine parameters comprises receiving three-dimensional wedging of junctional and peri-apical disk levels of the reconstructed three-dimensional spine morphology and a sum of three-dimensional wedging of all thoracic and lumbar disks of the reconstructed three-dimensional spine morphology.

16. The method of claim 12, wherein receiving the patient-specific 3D morphological spine parameters comprises receiving the axial intervertebral rotation computed for a superior vertebra of the reconstructed three-dimensional spine morphology relative to an inferior vertebra of the reconstructed three-dimensional spine morphology, the inferior vertebra adjacent the superior vertebra and the superior and inferior vertebrae each having defined therefor in of the reconstructed three-dimensional spine morphology a local axis plane comprising a first axis, the rotation computed by projecting the first axis of the superior vertebra onto the local axis plane of the inferior vertebra.

17. The method of claim 12, wherein receiving the patient-specific 3D morphological spine parameters comprises receiving the slenderness computed as a ratio of a height to a width of a body of each one of thoracic and lumbar vertebrae of the reconstructed three-dimensional spine morphology.

18. The method of claim 12, wherein receiving the patient-specific 3D morphological spine parameters comprises receiving the torsion obtained by computing a first sum of the axial intervertebral rotation for all vertebrae in a first hemicurvature of a main idiopathic scoliosis curve in the reconstructed three-dimensional spine morphology, a second sum of the axial intervertebral rotation for all vertebrae in a second hemicurvature of the main curve, and a mean of the first sum and the second sum, the first hemicurvature defined between an upper end vertebra and an apex of the main curve and the second hemicurvature defined between a lower end vertebra of the main curve and the apex.

19. The method of claim 11, further comprising querying a memory with at least one of the generated final Cobb angle prediction and the modelled progression curve to retrieve a selected one of a plurality of treatment options stored in the memory, each of the plurality of treatment options suitable for treating the idiopathic scoliosis and having associated therewith at least one of a range of final Cobb angles and a rate of change of idiopathic scoliosis curve progression, and outputting the final Cobb angle prediction and the selected treatment option.

20. A non-transitory computer readable medium having stored thereon program code executable by a processor for generating a final Cobb angle prediction for idiopathic scoliosis, the program code executable for:
receiving patient-specific data comprising 3D morphological spine parameters, a selected curve type, and a selected skeletal maturity;
applying the patient-specific 3D morphological spine parameters, a selected curve type, and a selected skeletal maturity to a predictive model based on 3D morphological spine parameters, curve type, and skeletal maturity;
modeling a progression curve of the idiopathic scoliosis from the predictive model; and
generating a prediction of the final Cobb angle from the progression curve.

* * * * *